United States Patent
Carlsson et al.

[11] Patent Number: 6,053,920
[45] Date of Patent: Apr. 25, 2000

[54] HOLDER ELEMENT FOR IMPLANTATION IN BONE TISSUE

[75] Inventors: Lennart Carlsson, Mölndal; Ulf Johansson, Onsala, both of Sweden; Mark B. Downing, Brierley Hill, United Kingdom; Paul D. Spraggs, London, United Kingdom; John R. Walliker, Cobham, United Kingdom

[73] Assignee: Nobel Biocare AB, Göteborg, Sweden

[21] Appl. No.: 09/043,290

[22] PCT Filed: Oct. 10, 1996

[86] PCT No.: PCT/SE96/01289

§ 371 Date: Jun. 12, 1998

§ 102(e) Date: Jun. 12, 1998

[87] PCT Pub. No.: WO97/13477

PCT Pub. Date: Apr. 17, 1997

[30] Foreign Application Priority Data

Oct. 12, 1995 [SE] Sweden ................... 9503555

[51] Int. Cl.[7] ................. A61B 5/04; A61N 1/00
[52] U.S. Cl. ............... 606/72; 606/75; 606/129; 600/378; 600/379; 607/116; 607/137
[58] Field of Search ............... 606/72, 73, 75, 606/129, 232; 604/93; 600/372, 373, 378, 561, 379; 607/116, 136, 137

[56] References Cited

U.S. PATENT DOCUMENTS

| | | | |
|---|---|---|---|
| 4,328,813 | 5/1982 | Ray | 607/139 |
| 4,892,108 | 1/1990 | Miller et al. | 607/116 |
| 5,261,914 | 11/1993 | Warren | 606/73 |
| 5,562,670 | 10/1996 | Brånemark | 606/73 |

OTHER PUBLICATIONS

Advances in Audiology, vol. 4, "Middle Ear Implant: Implantable Hearing Aids", 1988, pp. 47–48.

*Primary Examiner*—Michael Buiz
*Assistant Examiner*—David O. Reip
*Attorney, Agent, or Firm*—Pollock, Vande Sande & Amernick

[57] ABSTRACT

A holder of a biocompatible material for implantation in bone tissue for controlled receipt and positional fixation of equipment for electrical transfer of information. A cylindrical mounting part is for lying outside of the bone tissue and includes a mounting end and a smooth outer surface. A conical insertion part is for insertion into the bone tissue. The insertion part is narrower than the mounting part and includes an insertion end opposite the mounting end and tapers toward the insertion end at an angle of 0° to 10°. A conical intermediate part is between the mounting part and the insertion part. A plurality of retention elements are at least on the insertion part for providing good initial anchoring and stability to the holder and for permitting the holder to be mounted in a preprepared hole in the bone tissue without screwing the holder. A channel extends through the holder for receiving the equipment and connections to the equipment and including an exit opening in the insertion part.

21 Claims, 2 Drawing Sheets

HOLDER ELEMENT FOR IMPLANTATION IN BONE TISSUE

FIELD OF THE INVENTION

The invention relates to a holder element for the controlled receipt and positional fixation of equipment which is preferably utilizable for the electrical transfer of information, which element is intended to be implanted in bone tissue. The holder element consists of a tissue-friendly material and possesses a through channel which extends from the mounting end of the holder element up to that end which is intended to be inserted in the bone tissue (the insertion end) for the receipt of connections to the equipment.

BACKGROUND OF THE INVENTION

A holder element of this type, which is formed in a rotationally symmetrical manner, has been disclosed previously, see, for example, Swedish patent document SE 93.01406-6. They are principally intended to form a combined passage through the skin and controlled positional fixation of other equipment, for example equipment for transferring information to the inner ear in the case of persons having hearing difficulties.

In this context, the previously disclosed holder elements are based on the anchoring elements, or fixtures, which have been used with great success for supporting artificial teeth and teeth bridges, and also other prostheses such as artificial joints, in the case of joint reconstructions, etc. The above referenced patent publication describes just one example of such a holder element. In addition to the fact that the holder element described in the above Swedish patent document is formed in a rotationally symmetrical manner, it is provided with an external thread which extends from the insertion end up to the mounting end. The external thread increases the initial stability of the holder element during the implantation and, by means of providing the insertion end of the holder element with self-tapping slits, where the longitudinal edges of the slits are shaped as cutting edges, an increased grip is obtained against the walls in a hole which has previously been prepared in the bone tissue.

It is important for long-term anchorage stability that the material is tissue-friendly and preferably consists of titanium, with the titanium exhibiting a micropitted surface having a pit diameter of between 10 and 1000 nm, preferably 10 and 300 m. This creates the best conditions for a good, and consequently enduring, anchorage between the cell offshoots of the tissue and the micropits.

When the known holder element is being inserted by operation, the bone is exposed by dissection and a hole, whose depth corresponds to the intended depth of insertion and whose diameter principally corresponds to the internal diameter of the outer thread, is made in it. Since the holder is screwed into the prepared hole, leads and contact elements have to be passed into the holder and fixed there subsequently, since the leads would otherwise become twisted. The known holder element is therefore provided with a separate contact element whose position is fixed against an inner ring flange or shoulder. While it is true that it is stated that the contact element should sit well against the wall of the through bored-out hole, the additional gap which is formed between the contact element and the wall of the bored-out hole always constitutes a point of potential danger for bacterial ingrowth and for infections in association with passage through the skin.

It is difficult to fix the position of, and assemble, a contact element and other equipment in the holder element of the patient after the holder element has been mounted and there is a risk of the holder element being subjected to undesirable forces during the assembly so that the integration between the implant surface and the surrounding bone tissue is disturbed, resulting in there being a risk of the holder element becoming loose in the long term. There is, therefore, a need to produce a holder element which has as few parts as possible and which, when being mounted, is as preassembled as possible so that the risk of gaps and disturbances of the initial Stability is minimized.

When the holder element is used as a cochlear implant, it is placed in the bone behind the ear and includes equipment for transferring information to the inner ear. Contact leads pass through the through channel and are guided out through the insertion end of the holder and conducted to the inner ear. In this context, the contact leads have to be angled off at what is in principle 90° after they have left the holder element in order to ensure that they do not come too close to the meninges and risk damaging them. Even if the mastoid bone behind the ear is somewhat thicker than the remainder of the cranial bone, there can be a lack of space for passing the contact leads through in this way. It is true that it is intimated that, in the case of the known holder element, it should be possible to guide the contact leads out from the through channel by way of openings which are arranged in the casing surface of the holder element. However, it is not shown how this could is be done in practice, since the holder is screwed into the bone and the hole in the casing surface must in that case be matched with a corresponding hole in the bone adjacent to the opening in the casing surface. Furthermore, it is desirable to leave the bone adjacent to the casing surface of the holder as undisturbed as possible, on the one hand in order to ensure that the barrier against bacterial leakage remains as thick as possible. On the other hand it is desirable in order to avoid unnecessarily diminishing the surface which adjoins the bone and which is to be integrated with the bone.

SUMMARY OF THE INVENTION

The object of the present invention is to produce a holder element which provides a solution to the abovementioned disadvantages associated with previously disclosed holder elements, concomitantly rendering a holder element especially suitable for cochlear implants.

According to the present invention, at least that part of the holder element which is in contact with the bone tissue after implantation has a slightly conical shape and is provided with retention elements, preferably in the form of grooves. This enables the holder to be mounted without turning (screwing). The initial stability is nevertheless adequate, due to the retention elements and the slightly conical shape. The fact that the holder does not have to be screwed into the bone results, furthermore, in it being possible for the exit opening for the contact leads to be located asymmetrically so that the leads are guided out from the holder in a more favorable direction and do not have to be angled to such an extent after having left the holder.

The grooves preferably have a profile which corresponds to the screwing die profile of a conventional anchoring element, or fixture, for example of the type which is marketed by Nobel Biocare AB for dental applications under the trade mark Branemark System®. This creates the best possible conditions for ensuring that the holder element has good initial stability. The only difference as compared with the anchoring elements which have been used previously with great success is then, as far as the retention is concerned, that the grooves, in contrast to the screwing die, lack pitch.

According to an expedient embodiment, the through channel adjacent to the insertion end of the holder is angled so that it opens out by the side of the axis of symmetry of the holder.

In another embodiment, the whole of the slightly conical, rotationally symmetrical part of the holder is angled. This is also possible due to the holder being mounted without being screwed into the prepared hole in the bone. In this way, a further angling-off of the contact leads can already be achieved in the holder and without any exit opening having to be made in the casing surface of the holder element.

BRIEF DESCRIPTION OF THE INVENTION

The invention will be explained in more detail below with reference to the attached drawings, which show some examples of suitable embodiments, where FIGS. 1a and b show a side view, and a longitudinal section through the axis of rotation, respectively, of a first embodiment of a holder element according to the invention, FIG. 2 shows a longitudinal section through a second embodiment of the holder element, FIG. 3 shows how this second embodiment is expediently manufactured by making an oblique cut where the grooves end, after which the loose, cut-off part is turned through 180° and reunited with the remainder of the holder, FIG. 4 diagrammatically shows an application of the holder element in association with a cochlear implant, and FIG. 5 diagrammatically shows another application of the holder element in association with locating a contact lead under the skin.

DETAILED DESCRIPTION OF THE INVENTION

Figure 1A:
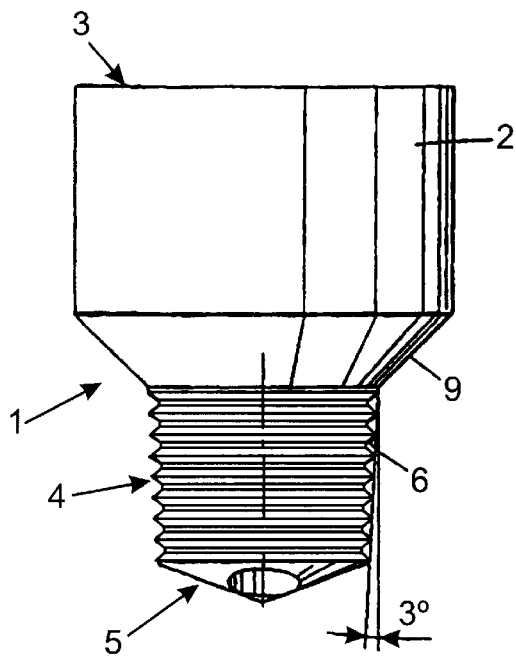
Figure 1B:
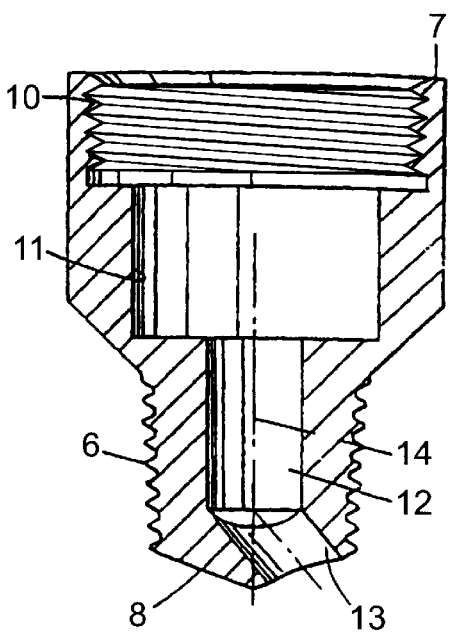

The holder element 1 shown in FIG. 1 includes a titanium body which is substantially cylindrical. The cylindrical body has a broader part 2 in association with its one end 3, the mounting end, and a narrower part 4 which extends up to the other end 5 of the holder, that is, the insertion end which is intended to be inserted into the bone tissue. While the broader part 2, which, after having been mounted, forms a passage through the soft tissue, the skin, has a smooth casing surface, the narrower part 4 possesses retention elements in the form of grooves 6 for the purpose of providing the holder with good initial stability in the bone tissue.

The narrower part 4 has a rotationally symmetrical casing surface which, along its whole length, tapers in a slightly conical manner towards the insertion end 5. The cone angle is between 1° and 5°, preferably 3°. The cone angle may be from 0° to 10°. This facilitates insertion of the holder into a hole which has previously been prepared in the bone.

The wider part 2 has a plane end surface 7 at its mounting end while the narrower part 4 is terminated by a somewhat pointed end surface 8. The cone angle of the pointed end surface is on the order of size of 70°.

The whole of the holder is made in one piece and the narrower part 4 merges into the wider part 2 by way of a comparatively short intermediate conical section 9, which is situated approximately in the middle of the holder.

The holder is provided with a through channel, which consequently extends through the whole of the holder from the mounting end 3 to the insertion end 5. The purpose of this channel is to receive leads and other equipment for signal transfer. The channel is formed by means of a number of bore holes having different diameters. The wider part 2 has a bore hole 10, 11 which has two different diameters and which forms space for contact elements and other equipment. The narrower part 4 has a narrower bore hole 12, which opens out at the slightly conical end surface 8 and is intended to accommodate contact leads which connect equipment outside the body with equipment, for example a cochlear implant, which is implanted in the body.

As FIG. 1 shows, the bore hole 12 is terminated by an angled part 13, so that the channel opens out at the side of the axis of symmetry 14 of the holder. In the example which is shown, the angled part 13 of the channel forms an angle of 40° with the axis of symmetry of the holder. This thereby results in a holder having an asymmetrical exit opening for the contact leads, something which is advantageous in the case of cochlear applications, in particular, where it is necessary to angle-off the contact leads after they have left the holder.

Figure 2:
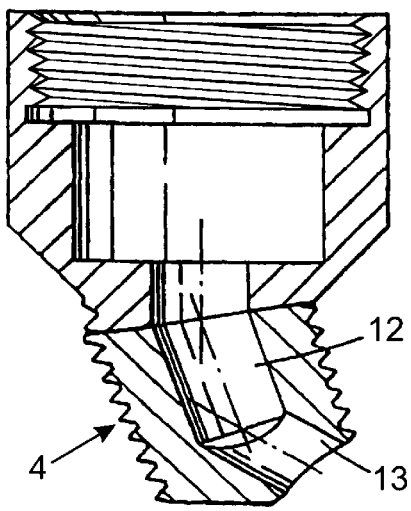

FIG. 2 shows a variant of the invention in which the whole of the narrower part 4 of the holder is angled. Such an angling is possible due to the fact that the holder is not screwed but pressed into the prepared hole in the bone. In this case, too, the channel 12 is terminated by an angled part 13. In this case, the narrower part 4 forms an angle of 20° with the axis of symmetry of the holder, which means, in turn, that the exit opening for the contact leads is angled-off by a total of 60°.

Figure 3:
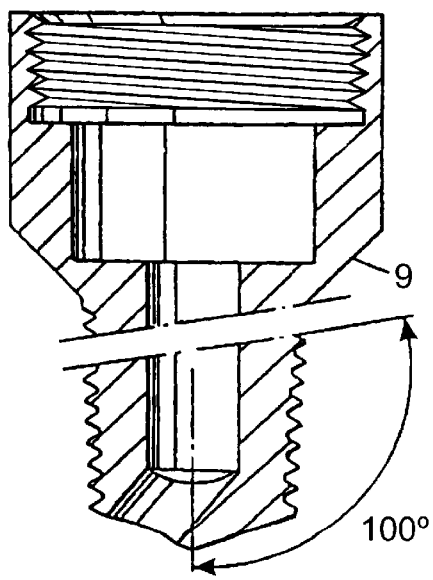

The holder shown in FIG. 2 is expediently manufactured from the holder 1 in FIG. 1, which is made in one piece. As FIG. 3 shows, the holder is cross-cut obliquely at the point where the grooves terminate in association with the conical central part 9, after which the cut-off part is turned through 180° and reunited with the remainder of the holder by means of laser welding. If the cross-cut is executed in such a way that it forms an angle of 100° with the axis of symmetry 14 of the holder, the finished holder according to FIG. 2 then has an insertion part which is angled at 20°. As has already been mentioned, the channel through the holder is angled off by a total of 60° through three different sections, thereby enabling the contact leads to be deflected in a gradual, gentle manner. Despite this relatively severe deflection, the exit opening for the contact leads is located on the end surface of the insertion end. This is advantageous since an opening does not have to be made in the casing surface of the holder and as thick a bone barrier as possible is retained, thereby decreasing the risk of bacterial leakage.

Figure 4:
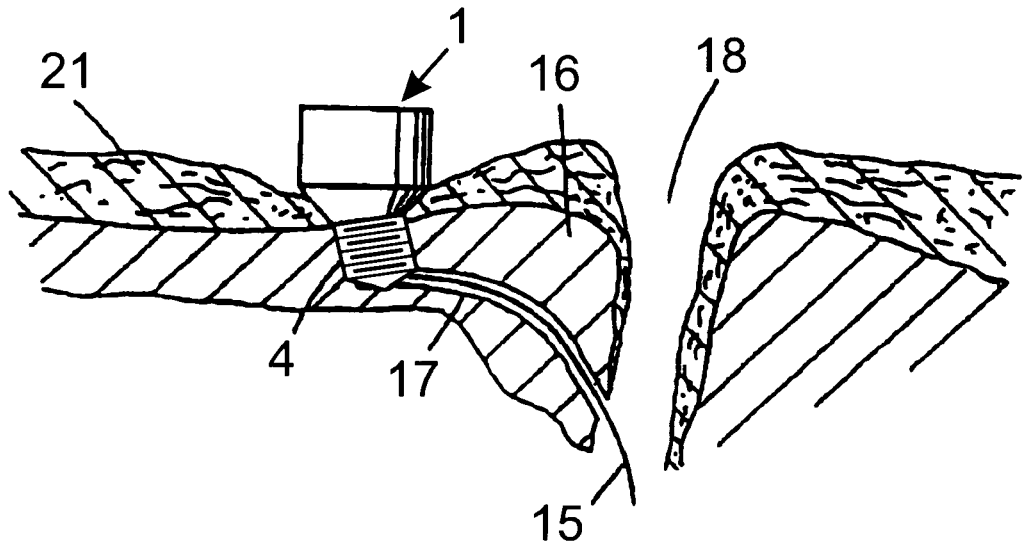

FIG. 4 diagrammatically shows an application of the holder in connection with a cochlear implant, that is, a hearing aid. The implant consists, in principle, of a microphone which converts sound vibrations into electrical signals. The signals are conducted through the holder element 1, via the contact leads 15, to electrodes which are fitted in the inner ear for the purpose of stimulating the auditory nerve so that the brain perceives sounds. The holder element is mounted behind the ear in the mastoid bone 16, or in the vicinity thereof, that is, in the rounded bone protuberance in the cranial bone which is located under the skin directly behind the ear. As can be seen from the figure, the holder in this case has an angled insertion part 4, which is angled towards the inner ear such that the leads are already pointing in the right direction when they leave the holder and are conducted in a channel 17 through the mastoid bone to the auditory meatus 18. Due to the fact that the holder does not have to be screwed into the preprepared hole in the bone, it is easy to orientate the holder so that the exit opening for the contact leads is in a favorable position.

Figure 5:
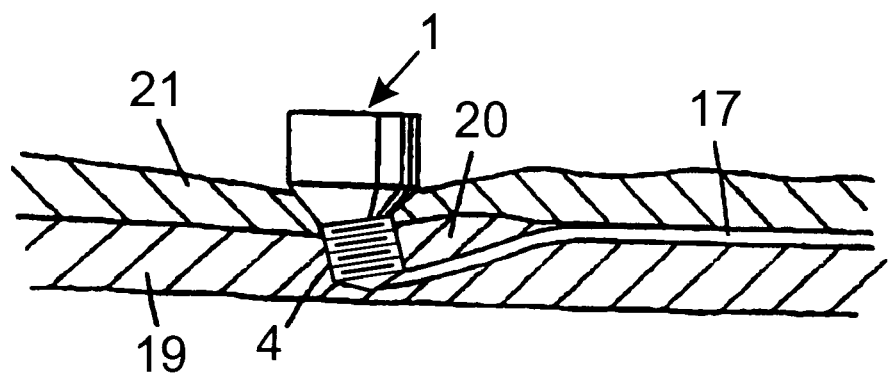

FIG. 5 shows an application of the holder 1 in which it is located in a relatively thin bone 19 and in which the contact leads are placed under the skin instead of being conducted through the bone into the inner ear as in FIG. 4. In such an application, it is important that the contact leads (the cable) are situated at a certain depth in the bone 19 when they leave the holder element so that there is a bone barrier 20, a seal, between the soft tissue 21 and the contact leads before they are allowed to ascend and pass under the skin. This decreases the risk of microbiological leakage along the cable. The angled, asymmetrically situated exit opening for the contact leads at the bottom of the holder element creates such a barrier, while, at the same time, the leads are already pointing away from the inner side of the bone when they leave the holder element so that they do not come too close to blood vessels, meninges or other delicate organs on the far side of the bone.

The invention is not limited to the embodiments which have been shown as examples and can be varied within the scope of the subsequent patent claims. In the example which has been shown above, the retention elements consist of grooves. It will be apparent that other types of retention element, such as a blasted surface or embossed surface, can also be used, provided that they allow the holder to be mounted in the preprepared hole without screwing.

We claim:

1. A holder of a biocompatible material for implantation in bone tissue for controlled receipt and positional fixation of equipment for electrical transfer of information, comprising:

a cylindrical mounting part for lying outside of the bone tissue and including a mounting end and a smooth outer surface;

a conical insertion part for insertion into the bone tissue, the insertion part being narrower than the mounting part and including an insertion end opposite the mounting end and tapering toward the insertion end at an angle of 0° to 10°;

a conical intermediate part between the mounting part and the insertion part;

a plurality of retention elements at least on the insertion part for providing good initial anchoring and stability to the holder and for permitting the holder to be mounted in a preprepared hole in the bone tissue without screwing the holder; and a channel extending through the holder for receiving the equipment and connections to the equipment and including an exit opening in the insertion part.

2. The holder according to claim 1, wherein the retention elements comprise a plurality of grooves.

3. The holder according to claim 1, wherein the channel is wider in the mounting part than in the insertion part.

4. The holder according to claim 1, wherein the exit opening of the channel is in the vicinity of the insertion end of the holder.

5. The holder according to claim 1, wherein the channel includes an angled portion such that the exit opening is arranged asymmetrically with respect to a longitudinal axis of the holder.

6. The holder according to claim 5, wherein the angled portion of the channel is angled 40° with respect to a longitudinal axis of the insertion part.

7. The holder according to claim 5, wherein the angled portion of the channel is angled 60° with respect to a longitudinal axis of the mounting part.

8. The holder according to claim 1, wherein a portion of the insertion part is angled with respect to the mounting part.

9. The holder according to claim 8, wherein an angled portion of the channel is angled 40° with respect to a longitudinal axis of the mounting part.

10. The holder according to claim 8, wherein a longitudinal axis of the insertion part is angled 20° with respect to a longitudinal axis of the mounting part.

11. The holder according to claim 7, wherein the insertion part is angled with respect to the mounting part.

12. The holder according to claim 1, wherein the mounting end is planar.

13. The holder according to claim 1, wherein a portion of the channel is threaded.

14. The holder according to claim 13, wherein the threaded portion of the channel lies in the mounting part.

15. The holder according to claim 1, wherein the channel includes an angled portion such that the exit opening is arranged asymmetrically with respect to a longitudinal axis of the insertion part.

16. The holder according to claim 1, wherein the conical insertion part tapers toward the insertion end at an angle of 1° to 5°.

17. The holder according to claim 1, wherein the conical insertion part tapers toward the insertion end at an angle of 3°.

18. The holder according to claim 1, wherein the insertion end has a conical surface.

19. The holder according to claim 18, wherein the conical surface of the insertion end tapers at an angle of 70°.

20. The holder according to claim 1, wherein the equipment comprises a cochlear implant.

21. The holder according to claim 1, wherein the retention elements comprise a blasted or embossed surface on the insertion part.

* * * * *